United States Patent [19]

Hooykaas et al.

[11] Patent Number: 5,635,381
[45] Date of Patent: Jun. 3, 1997

[54] AGROBACTERIUM BACTERIA CAPABLE OF SITE-SPECIFIC RECOMBINATION

[75] Inventors: Paul J. J. Hooykaas, Leiden, Netherlands; Teresa Mozo, Berlin, Germany

[73] Assignee: Mogen International NV, Leiden, Netherlands

[21] Appl. No.: 290,933

[22] PCT Filed: Feb. 25, 1993

[86] PCT No.: PCT/EP93/00463

§ 371 Date: Jan. 20, 1995

§ 102(e) Date: Jan. 20, 1995

[87] PCT Pub. No.: WO93/17116

PCT Pub. Date: Sep. 2, 1993

[30] Foreign Application Priority Data

Feb. 26, 1992 [NL] Netherlands ............... 922005582

[51] Int. Cl.$^6$ ............... C12N 15/82; C12N 15/84; C12N 5/04; A01H 5/00
[52] U.S. Cl. ............... 435/172.3; 435/71.2; 435/199; 435/252.2; 435/252.3; 435/320.1; 435/419; 536/23.72
[58] Field of Search ............... 435/71.2, 172.3, 435/199, 240.4, 252.2, 252.3, 320.1; 800/205, 250; 536/23.72

[56] References Cited

U.S. PATENT DOCUMENTS 5,102,797 4/1992 Tucker et al. ............... 435/172.3

OTHER PUBLICATIONS

Craig, N.L. "The Mechanism of Conservative . . . " Annu. Rev. Genet. (1988) 22:77–105.

Hobbs, S.L.A et al. "Transgene, Copy Number . . . " Plant Molecular Biology 21:10–26(1993).

Matzke M.A. et al. "How and Why do Plants. . . " Plant Physiol. (1995) 107:679–685.

Odell et al. 1990 Md. Gren. Genet. 223(3):369–378.

Odell et al. 1994, pp. 219–270 In: Homologues and Gene Silencing in Plants, Paszkowski, J. (ed.), Kluwer Academic Publishers: The Netherlands.

Horsch et al. 1984. Science 223: 496–498.

DeBlock et al. 1984 EMBO J 3(8):1681–1689.

Sauer et al. 1987, Proc. Natl. Acad. Sci. USA 84:9108–9112.

*Primary Examiner*—David T. Fox
*Attorney, Agent, or Firm*—Ladas & Parry

[57] ABSTRACT

The invention provides Agrobacterium strains capable of producing a cite-specific recombinase capable of effecting site-specific recombination of a first and a second recombination site in Agrobacterium strains, when present therein, comprising a structural DNA sequence encoding said recombinase and a DNA sequence capable of controlling expression in Agrobacterium strains. The invention also provides methods for using the strains to transform plant cells.

20 Claims, 9 Drawing Sheets

AGROBACTERIUM BACTERIA CAPABLE OF SITE-SPECIFIC RECOMBINATION

FIELD OF THE INTENTION

The invention concerns Agrobacterium strains which harbor recombinant DNA and which are capable of site-specific recombination, a method for obtaining said Agrobacterium strains, and methods of use of said Agrobacterium strains.

BACKGROUND OF THE INVENTION

Agrobacterium is a genus of gram-negative soil bacteria which cause neoplastic cell growth in dicotyledonous plants by means of the natural system they possess for transferring phytohormone-producing DNA to plant cells. The T-(transferred)region is a segment of the large so-called Ti-(tumour inducing)plasmid (200 kb) harbored by all virulent Agrobacterium strains. (Occasionally, the T-region is also referred to as T-DNA.) Mobilization of the T-region to the plant cells is mediated by another region of the Ti-plasmid, which is called the vir-(virulence)region, in a process that resembles bacterial conjugation (see for reviews: Melchers LB and Hooykaas PJJ (1987) In: Miflin BJ (ed) Oxford surveys of plant and cell biology, vol 4. Oxford Univ Press, London/New York, pp 167–220; Zambryski P (1988) Annu. Rev. Genet. 22:1–30; Zambryski P, Tempe J, Schell J (1989) Cell 56:193–201).

This natural gene transfer system can be used to co-transfer DNA not naturally present in the T-region. The T-region is flanked by two 24 bp imperfect direct repeats (T-DNA borders) which are the only cis-essential elements for the transfer process; i.e. the borders must be linked to the DNA to be transferred to the plant cell. An ideal vector system for transferring DNA to plant cells should comprise the DNA to be transferred into the plant cell flanked on both sides by T-DNA borders, although it has been established that the right T-DNA border, preferably in conjunction with a region just outside the T-region and referred to as "overdrive", suffices for the transfer of DNA. Although not essential, the presence of this overdrive increases the efficiency of transfer of the DNA flanking the right border.

The second essential element, the vir region, can be provided in trans, i.e. not physically linked to the T-region. This finding has originated in the development of a binary vector system, in which the T-region, comprising DNA to be co-transferred to the plant cell, is cloned into a broad-host-range plasmid which is capable of replication in Agrobacterium and E. coli, while the vir functions are supplied by a disarmed helper plasmid which does not contain a T-region (Hoekema A, Hirsch PR, Hooykaas PJJ, Schilperoort RA (1983) Nature 310:115–120; European Patent EP-B 120 516); Bevan M (1984) Nucl. Acids. Res. 22:8711–8721). A binary vector system wherein the T-region is located on the chromosome of the Agrobacterium strain has also been disclosed (EP-B 176 112).

Although a binary vector system is very versatile, broad-host-range plasmids are less suitable as routine cloning vectors; they are large and generally have a low copy number. Moreover, they are usually unstable in Agrobacterium in the absence of selective pressure.

As an alternative to a binary vector system, one can use a so-called cointegrate system. Typically, the vir-functions reside on a Ti-plasmid and the DNA to be co-transferred has to be recombined into this Ti-plasmid. All cloning steps can be done using an E. coli vector, whereafter this vector is introduced into Agrobacterium, for instance by triparental mating or electroporation. Subsequently, homologous recombination between the vector and the acceptor Ti-plasmid has to take place, via a single or double crossover, employing large regions of homology between the E. coli vector and the acceptor Ti-plasmid. The regions of homology can for instance be engineered into the acceptor Ti-plasmid by replacing the DNA originally comprised between the T-DNA borders on said plasmid with cloning vector sequences, such as pBR322 (Van Haute E, Joos H, Maes M, Warren G, Van Montagu M, Schell J. (1983) EMBO J. 2:411–418; Zambryski P, Joos H, Genetello C, Leemans J, Van Montagu M, Schell J. (1983) EMBO J 12:2143–2150; Deblaere R, Bytebier B, De Greve H, deboeck F, Schell J, Van Montagu M, Leemans J (1985) Nucl Acids Res 13:4777–4788). It is also possible to employ helper plasmids which are free of T-DNA borders as acceptor plasmids; in this case it will be necessary to provide at least the right T-DNA border operably linked to the DNA to be introduced into a plant cell on the cloning vector. A disadvantage of this system is that homologous recombination, especially the favor double crossing over, is not a very efficient and precise process in Agrobacterium strains, necessitating tedious selection of the cells harboring the desired cointegrates, before they can be used in plant transformation. An additional disadvantage of the resulting cointegrate plasmids resides in the fact that large regions of repetitive sequences occur, which may cause instability.

It is possible to perform the recombination steps in E. coli instead of Agrobacterium, as described in EP-B 120 515, and subsequently transferring the cointegrate plasmid to Agrobacterium for use in plant transformation.

It would be advantageous if recombination can be performed in Agrobacterium, without the need for large regions of homology between the acceptor plasmid and the cloning vector.

STATE OF THE ART

Genetic recombination can be broadly divided into two categories: homologous recombination and site-specific recombination. With homologous recombination the actual site of recombination is not predictable in advance; large regions of homology are necessary to achieve recombination at a reasonable frequency, whereas with site-specific recombination the recombination site is precisely known; moreover, no extensive regions of homology are needed (for review: Craig et al., (1988) Annu. Rev. Genet. 22, 77–105).

A Cre-loxP site-specific recombination system of E. coli phage P1 has been disclosed (Sternberg N and Hamilton D (1981) J Mol Biol 150:467–486.); (lox: locus for recombination—P—from phage P1; cre: causing recombination). The Cre recombinase recognizes the 34 bp loxP DNA sequence consisting of two 13 bp inverted repeats separated by a 8 bp non-symmetric sequence, and promotes its recombination with another loxP sequence. When the two loxP sites are present in different circular DNA molecules, the recombination event causes their cointegration, while when the two loxP sites are in the same molecule, depending on their relative orientation (direct or inverted), the DNA lying in between is either excised or inverted (Abremski K, Hoeas R, Sternberg N (1983) Cell 32: 13011–1311; Hoess RH, Wierzbicki A, Abremski K (1986) Nucl Acids Res 14: 2287–2300).

The system has been shown to work in yeasts (Sauer B (1987) Mol Cell biol 7:2087–2096) and mouse cultured cells (Sauer B and Henderson N (1989) Nucl. Acids. Res. 17:147–161.) and recently, it has been used for site-specific recombination in the genome of transgenic tobacco (Odell J, Caimi P, Sauer B, Russel S (1990) Mol Gen Genet 203:3669–378; International Patent Application WO91/09957).

Similar recombination systems, requiring only a single polypeptide enzyme and short specific DNA sequences (recombination sites) have been reviewed by Craig et al. (supra).

It is an object of the invention to provide Agrobacterium strains and vectors for use therein, which are capable of site-specific recombination, allowing for insertion of DNA not naturally present in said Agrobacterium strains.

SUMMARY OF THE INVENTION

The invention provides Agrobacterium strains capable of producing a site-specific recombinase capable of effecting site-specific recombination of a first and a second recombination site in Agrobacterium strains, when present therein, comprising a structural DNA sequence encoding said recombinase and a DNA sequence capable of controlling expression in Agrobacterium strains.

The invention also comprises Agrobacterium strains which further contain a first recombination site.

The invention further provides a method for producing a site-specific cointegrate in an Agrobacterium strain, comprising the steps of introducing into an Agrobacterium strain which contains a first recombination site a DNA molecule harboring a second recombination site compatible with said first recombination site, and effecting production of the site-specific recombinase in said Agrobacterium strain.

According to a preferred embodiment of the invention the said Agrobacterium strain harbors vir-functions, and said DNA molecule harboring a second recombination site comprises DNA not naturally present in a plant cell positioned to a right T-DNA border, or positioned between a left and a right T-DNA border, so as to allow co-transfer of said DNA with said right T-DNA border.

The invention further comprises site-specific cointegrates and Agrobacterium strains comprising said site-specific cointegrates.

The invention further comprises a method for obtaining a plant cell containing DNA not naturally present therein, comprising the steps of contacting plant cells with an Agrobacterium strain harboring a site-specific cointegrate comprising virulence functions and DNA not naturally present in a plant cell positioned to a right T-DNA border, or positioned between a left and a right T-DNA border, so as to allow co-transfer of said DNA with said right T-DNA border, and selecting a plant cell having obtained said DNA not naturally present therein.

The invention further provides plant cells and plants as well as products and extracts obtained using a method according to the invention.

The invention further comprises Agrobacterium strains which comprise two compatible recombination sites which are in the same orientation and on the same molecule, so that upon production of the recombinase in said Agrobacterium strains recombination is effected and the DNA in between the recombination sites is excised from said vector.

In another embodiment of the invention the latter Agrobacterium strains comprise two compatible recombination sites which are in the opposite orientation and on the same molecule, so that upon production of the recombinase in said Agrobacterium strains recombination is effected and the DNA flanked by the recombination sites is inverted in said molecule.

In a preferred embodiment of the invention said structural DNA sequence is acre coding gene sequence or a functional variant or portion thereof, and said DNA recombination site is a loxP locus, or functional variant or portion thereof.

column A, B and C represent Agrobacterium strains having the cre⁺ phenotype, e.g. by virtue of the presence of the cre recombinase gene on an incP plasmid (not drawn), or on a stable DNA molecule in Agrobacterium, provided that expression can be regulated through a represssor, an inducer or both; Roman figures represent process steps; Column B represents Agrobacterium strains obtained by either one of the process steps I–VI. Step VII indicates three alternatives (a)–(c) for changing the cre⁺ phenotype into a cre⁻ phenotype (absence of the recombinase); (a) represents adding a repressor to silence otherwise constitutive expression of the recombinase gene; (b) represents the removal of an inducer of an otherwise repressed expression of the recombinase gene; and (c) represents the removal of the recombinase gene by removal of a plasmid that is unstable in said Agrobacterium strains.

Figure 9:
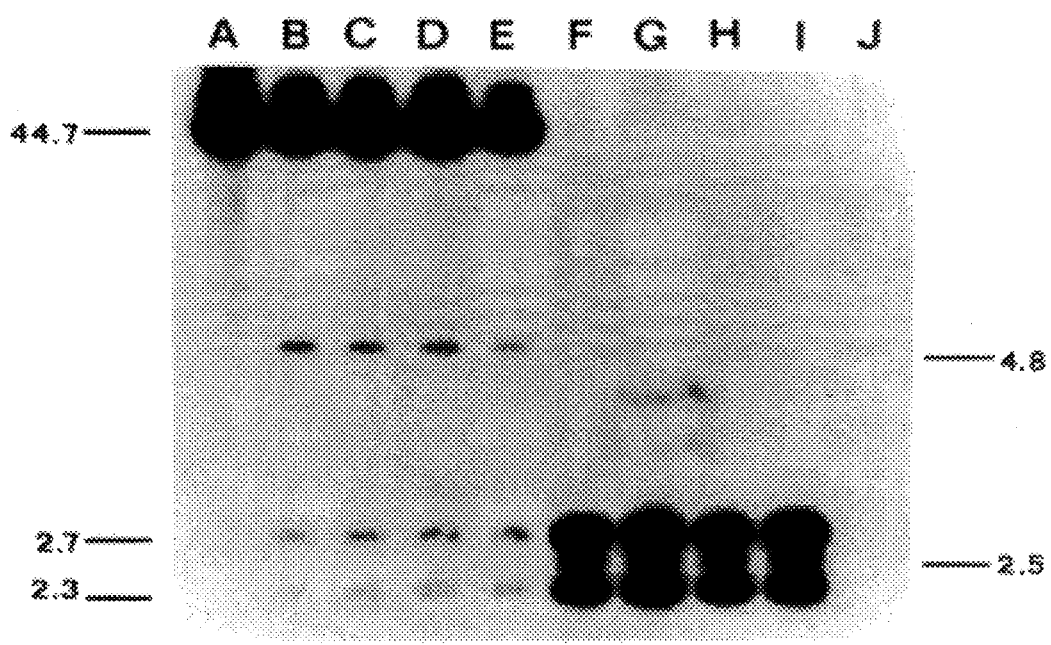

FIG. 9 is a autoradiograph of a Southern blot, showing the results obtained with the cointegrate experiments; for more detailed explanation see Example III-B.

DETAILED DESCRIPTION OF THE INVENTION

The steps that led to the findings of the present invention, as well as a number of the various ways of practicing the invention are worked out below, in more detail.

To establish whether it was possible to obtain Agrobacterium strains capable of site-specific recombination, the site-specific recombinase Cre and the recombination site loxP were tested in *Agrobacterium tumefaciens*.

A DNA fragment encoding the structural coding sequence of the cre gene was cloned and positioned under the control of the promoter from the lac-operon from *E. coli*. This promoter is inducible in *E. coli* but known to be constitutive in the absence of the repressor in Agrobacterium. This cre gene construct was cloned into an incP plasmid, pNJ5000, yielding pRL756, which appeared unstable in *Agrobacterium tumefaciens* strain MOG101 in the absence of tetracycline or carbenicillin.

As a first substrate molecule for Cre-mediated site-specific recombination a disarmed (without T-region) helper plasmid was constructed from pTiB6. This was done in *Agrobacterium tumefaciens* strain LBA1010, by exchanging the T-region from pTiB6 with a DNA fragment containing a loxP-site and a spectinomycin marker gene, via homologous recombination (double crossing-over), employing regions of homology outside the T-DNA borders on pTiB6. This plasmid, derived from pTiB6, now harboring the vir-functions for T-DNA transfer to plant cells, a loxP locus, the spectinomycin marker and no T-DNA borders, was called pAL1166. To establish that Cre-mediated site-specific recombination between the loxP site of pAL1166 and a loxP site of a second DNA molecule can indeed take place in *Agrobacterium tumefaciens*, a second DNA molecule, pRL754 harboring a loxP site and a kanamycin resistance gene under the control of a promoter on a plasmid derived from pIC20H, was introduced into Agrobacterium strain that harbored both pRL756 and pAL1166, and cointegrate formation was checked by selecting for kanamycin resistance. In the absence of the Cre plasmid pRL756, which was removed in the absence of selection for Carbenicillin and Tetracycline, the cointegrates appeared stable.

From these experiments it was concluded that Cre-mediated site-specific recombination between a first and a second loxP site is a very efficient process in *Agrobacterium tumefaciens*, and that the cointegrates remain stable, which opens new perspectives for the introduction of DNA into Agrobacterium which is not naturally present therein.

To find out whether cointegrates obtained via Cre-mediated site-specific recombination can also be used for plant transformation, the above experiment was repeated in a slightly modified way. Into plasmid pRL754, shown to be cointegrated into pAL1166 in the above experiment, a DNA fragment containing a left T-DNA border, a plant expressible kanamycin resistance gene under the control of the promoter of the nopaline synthase gene of *Agrobacterium tumefaciens*, and a right T-DNA border. This plasmid was introduced into the *Agrobacterium tumefaciens* strain harboring the Cre plasmid pRL756 and plasmid pAL1166, and strains harboring Cre-mediated site-specific cointegrates were selected as above.

To assess whether Agrobacterium strains harboring these site-specific cointegrates are capable of co-transferring the plant expressible kanamycin resistance gene located between the T-DNA borders to plant cells, the Km resistant Agrobacterium strains were used for transformation of tobacco plants. It was found that Agrobacterium strains harboring these site-specific cointegrates were equally capable of effective transfer of T-DNA to plant cells as comparable strains harboring the same manipulated T-region on binary vectors.

Transformed tobacco plants are now grown to maturity and allowed to set seed. It is predicted that the stability of the kanamycin resistant phenotype does not differ from conventionally transformed plants, and that the trait is transferred to the progeny.

It will be clear from the experiments above that site-specific recombination makes Agrobacterium a more versatile system, both if used as a plant transformation system and as a host for foreign DNA expression per se.

DNA to be introduced into Agrobacterium, e.g. modified T-regions for plant transformation harboring gene cassettes to be transferred to plant cells, or genes meant to be expressed in Agrobacterium itself, can be cloned suitably in small and sophisticated cloning vectors for any suitable host, said vectors only requiring to comprise a recombination site, which is easily inserted into said vector as a small DNA fragment.

Since this site-specific recombination system is completely independent of conventional homologous recombination, large regions of hemology are not necessary to achieve recombination, and one can even work in an Agrobacterium strain that is deficient for homologous recombination (rec⁻), thus further reducing the occurrence of unwanted rearrangements which may be due to coincidental regions of hemology.

Figure 8:
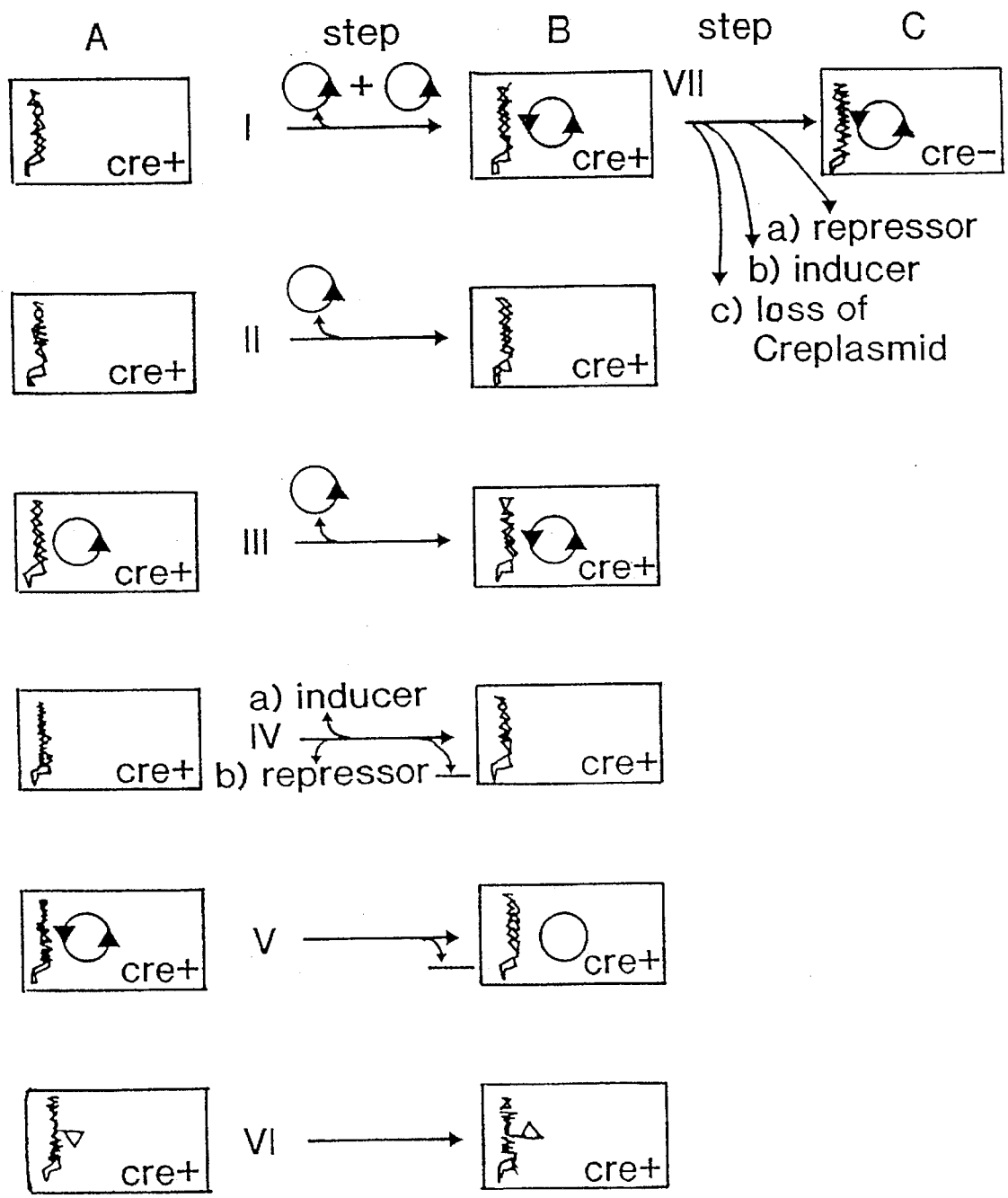
FIG. 8 represents a—non-exhaustive—overview of the various possibilities that are offered by the present invention.

As is reflected diagrammatically in FIG. 8, site-specific recombination according to the invention is intended to cover both cointegration, excision and inversion.

Cointegration, whereby at least two DNA molecules recombine to form at least one larger DNA molecule, is reflected in steps I, II, and III. Step I indicates the possibility to simultaneously introduce into Agrobacterium at least two DNA molecules capable of site-specific recombination. In this particular situation at least one of both DNA molecules should contain an origin of replication that is functional in Agrobacterium, should it be desired that the cointegrate is stably maintained therein; steps II and III indicate the formation of a cointegrate where at least one DNA molecule is resident and another DNA molecule is newly introduced, whereby the resident DNA molecule in step II is a chromosome of Agrobacterium, and in step III the resident molecule is a plasmid. Obviously, this is not indicated, it would be possible to introduce DNA molecules into cre⁻ Agrobacterium strains, and furnish the Cre-recombinase for instance by introducing a plasmid containing the gene, simultaneously, or after the introduction of the said DNA molecules.

Step VII is a preferred step for stabilizing a formed site-specific cointegrate obtained after steps such as I–III; (a) refers to adding to Agrobacterium a repressor for the cre-gene, alternatively, or additionally (b) the inducer of normally repressed gene can be removed, or (c) the gene encoding the Cre-recombinase can removed in its entirety by allowing an unstable plasmid to become lost from the Agrobacterium strains.

Steps IV–VI indicate the possibility to excise or invert fragments of DNA between two recombination sites.

According to a preferred embodiment of the invention the Agrobacterium strains according to the invention are used as a transfer system of DNA to plant cells.

Preferred DNA to be transferred to plant cells are genes encoding protein, and a expression controlling DNA sequence such that upon expression of the gene the protein is produced in a plant or plant cell at the desired stage and at the desired site in the plant. The gene of interest may also comprise genes which can be expressed in the form of an RNA sequence which does not encode protein, such as antisense genes, ribozyme genes and the like. The gene of interest not necessarily needs to be capable of being transcribed; it may as well be a recognition sequence that can be recognized by proteins, e.g. a recombinase, a nuclease and the like, or by man, serving as a genetic label.

More specific examples of the use of a gene of interest include but are not limited to those involved with fungal resistance (EP-A 392 225, International Patent Application WO90/07001; EP-A 440 304), insect resistance (EP-A 193 259), nematode resistance (EP-A 352 052), virus resistance (EP-A 223 452), altered carbohydrate composition (WO90/12876; EP-A 438 904), altered oil composition (EP-A 225 377), seed storage proteins with altered amino acid composition (EP-A), male sterility (EP-A 329 308), modified flower color (EP-A 335 451), delayed fruit ripening (WO91/01375), salt resistance (WO91/06651), herbicide resistance (EP-A 218 571; EP-A 369 637), production of pharmaceutical products (EP-A 436 003) and the like.

Suitable DNA sequences for control of expression of genes of interest, or marker genes, such as promoters, enhancers, non-transcribed leaders and the like, may be derived from any gene that is expressed in a plant cell, including plant genes (EP-122 791), genes located on wild-type T-DNA of Agrobacterium (EP-A 126 546), plant virus genes (EP-B 131 623), including functional portions, hybrids, or synthetic copies thereof.

To select or screen for transformed cells, it is preferred to include marker genes linked to the gene of interest in the T-region that is to be transferred to the plant cell. The choice of a suitable marker gene in plant transformation is well within the scope of the average skilled worker; some examples of routinely used marker genes are the neomycin phosphotransferase genes conferring resistance to kanamycin (EP-B 131 623), the Glutathion-S-transferase gene from rat liver conferring resistance to glutathion derived herbicides (EP-A 256 223), glutamin synthetase confering upon overexpression resistance to glutamine synthetase inhibitors such as phosphinotricin (WO87/05327), the acetyl transferase gene from *Streptomyces viridochromogenes* conferring resistance to the selective agent phosphinotricin (EP-A 275 957), the gene encoding a 5-enolshikimate-3-phosphate synthase (EPSPS) conferring tolerance to N-phosphonomethylglycine, the bar gene conferring resistance against Bialaphos (e.g. WO91/02071) and the like. The actual choice of the marker is not crucial as long as it is functional (i.e. selective) in combination with the plant cells of choice.

The marker gene and the gene of interest do not have to be linked, since co-transformation of unlinked genes (U.S. Pat. No. 4,399,216) is also an efficient proces in plant transformation.

Transformed cells obtained and selected according to the invention may be used as such, for instance for the production of a pharmaceutical compound in cell suspension cultures, or used to generate a whole new plant.

The choice of plant material for obtaining transformed plant cells and/or generation of whole new transformed plants is not critical to this invention as long as it is amenable to T-DNA transfer by Agrobacterium strains.

Especially preferred plant material, especially for dicotyledonous crops are leaf-discs which can be readily transformed and have good regenerative capability (Horsch R. B. et al., (1985) Science 227, 1229–1231).

Monocotyledonous plants are amenable to DNA transfer by Agrobacterium strains (EP-B 159 418), including commercially important crops such as corn (Gould J, Michael D, Hasegawa O, Ulian EC, Peterson G, Smith RH, (1991) Plant. Physiol. 95, 426–434).

Recent reports suggest that Agrobacterium mediated DNA transfer may be combined with tissues that have been wounded by microprojectile bombardment (Bidney D, Scelonge C, Martich J, Burrus M, Sims L, Huffman G, (1992), Plant Mol Biol 18, 301–313).

It should be clear that the Agrobacterium strains according to the invention can be used for plant transformation just as 'conventional' Agrobacterium strains using the same techniques as employed with conventional Agrobacterium strains. It is therefore clear that alternative ways of using Agrobacterium for plant transformation, not explicitly mentioned here, do not depart from the scope of the invention.

All references cited in this specification are indicative of the level of skill in the arts to which the invention pertains. All publications, whether patents or otherwise, referred to previously or later in this specification are herein incorporated by reference as if each of them was individually incorporated by reference.

The Examples given below are just given for purposes of enablement and do not intend in any way to limit the scope of the invention.

EXPERIMENTAL

Bacterial Strains, Plasmids and Bacteriophage

Figure 1:
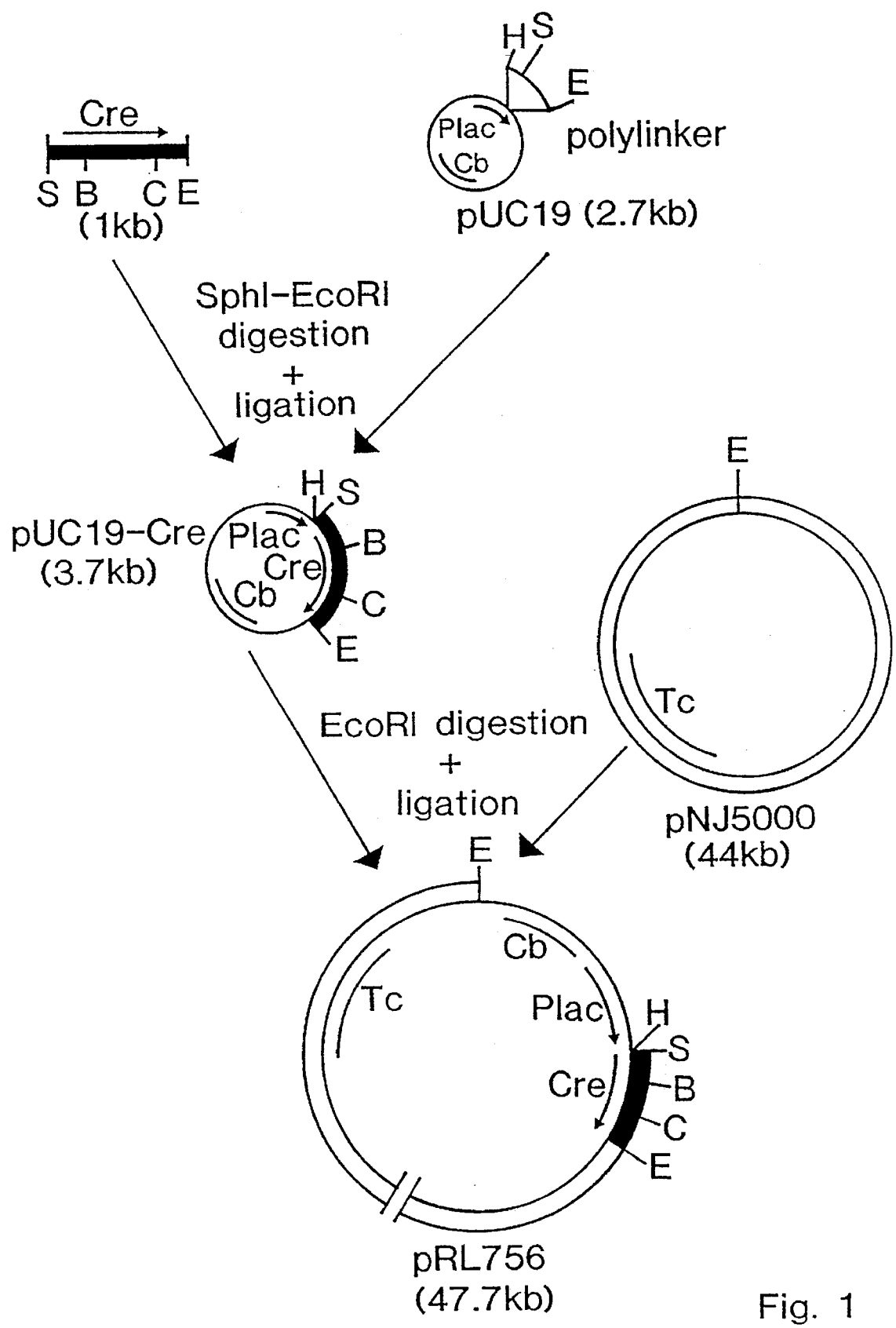
FIG. 1 shows schematically the construction of pRL756, harboring the cre structural coding sequence under the control of the promoter from the lac-operon from E. coli, a tetracyclin resistance gene and a carbenicillin resistance gene on a plasmid which is unstable in Agrobacterium in the absence of selection.
Figure 2:
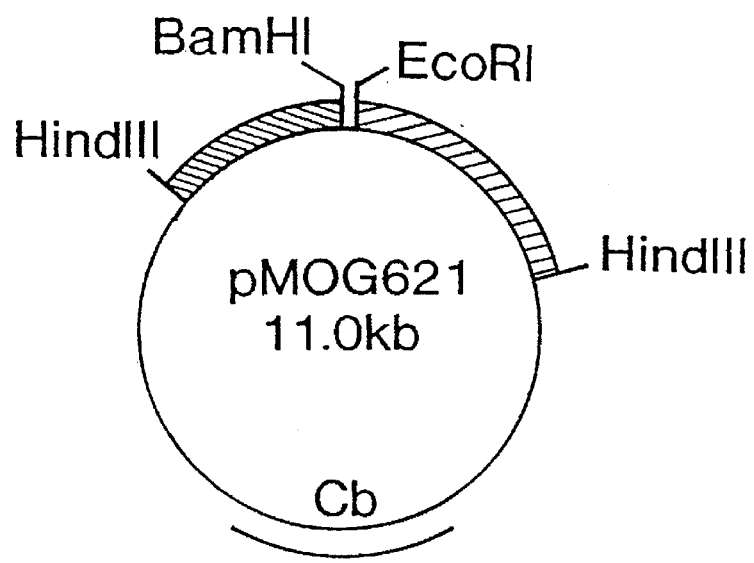
FIG. 2 shows the relevant features of pMOG621 and pMOG579.
Figure 2:
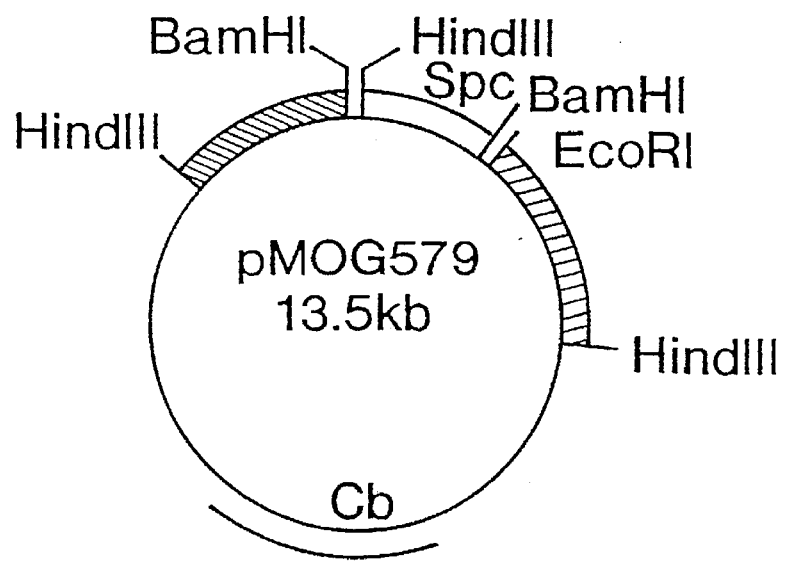
Figure 3:
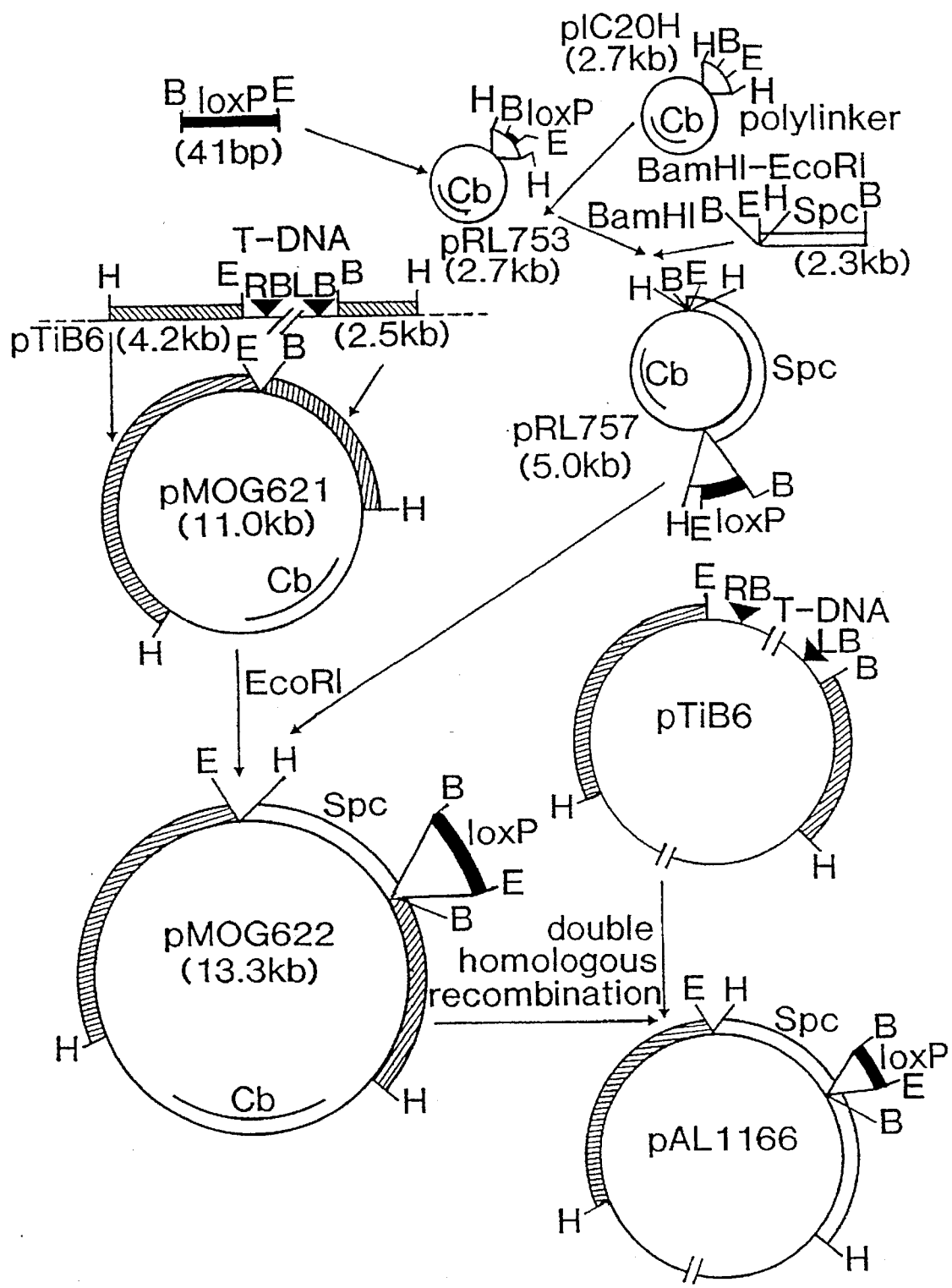
FIG. 3 shows schematically the construction of pAL1166, harboring the vir-functions from pTiB6 and in which the T-region (including the T-DNA borders), has been exchanged with a DNA fragment containing a spectinomycin resistance gene and a loxP recombination site, via homologous recombination. This plasmid is useful for obtaining site-specific cointegrates which may subsequently be used for the transfer of DNA to plant cells. Since pAL1166 no longer contains T-DNA borders, a second DNA molecule containing the DNA to be introduced into plant cells should also provide at least a right T-DNA border operably linked thereto.

*E. coli* MH1 (Goddard JM, Caput D, Williams SR, Martin Jr DW (1983) Proc Natl Acad Sci U.S.A. 80:4281–4285) and JM101 (Yanisch-Perron C, Vieira J, Messing J (1985) Gene 33:103–119) were used for cloning. *A. tumefaciens* strains were: LBA1010 (C58, pTiB6, Rif) (Koekman et al., (1982) Plasmid 7, 119–132), MOG1010 (derived from LBA1010 by substitution of the T-DNA by a spectinomycin marker) and UIA143 (C58 recA mutant, pTi-cured, Ery) (Farrand SK, O'Morchoe SP, McCutchan J (1989) J Bacteriol 171: 5314–5321). Plasmids used in this work were: pUC19 (Yanisch-Perron et al. 1985, supra), pIC20H (Marsh JL, Erfle M, Wykes EJ (1984) Gene 32:481–485; FIG. 3), pHP45ΩKm (pBR322 derivative containing a kanamycin gene) (Fellay R, Frey J, Krisch H (1987) Gene 52:147–154).

pMOG621 (pBR322 derivative containing two pTiB6 T-DNA flanking fragments), pMOG579 (pMOG621 with a spectinomycin cassette separating the two pTiB6 fragments; FIG. 2), pNJ5000 (RP4 unstable derivative, Tc; FIG. 1) (Grinter NJ (1983) Gene 21:133–143), pBIN19 (incP binary vector, Km) (Bevan, 1984, supra), and pRK2013 (Ditta G, Stanfield S, Corbin D, Helinski D (1980) Proc Natl Acad Sci U.S.A. 77:7347–7351). P1 phage used was P1clr100Cm.

Culture Conditions

E. coli cells were grown in LC medium (Hooykaas PJJ, Klapwijk PM, Nuti MP, Schilperoort RA, Rorsch A (1977) J Gen Microbiol. 98:477–484) at 37° C. (P1 containment cells). Antibiotics were added to the following concentrations: carbenicillin, 100 µg/ml; kanamycin, 25 µg/ml; spectinomycin, 50 µg/ml; tetracycline, 5 µg/ml; cloramphenicol, 50 µg/ml. Agrobacterium strains were grown in LC medium (Hooykaas et al, 1977, supra) at 29° C. Antibiotic concentrations used were; carbenicillin, 75 µg/ml; kanamycin, 100 µg/ml; spectinomycin, 250 µg/ml; tetracycline, 2 µg/ml; rifampicin, 20 µg/ml; erythromycin, 100 µg/ml.

DNA Procedures

DNA isolation from E. coli, restriction, ligation, transformation, nick-translation of probes, and Southern blot to nitrocellulose filters were performed according to standard techniques (Sambrook J. Fritsch EF, Maniatis T (1989) Molecular cloning: a laboratory manual, second edition. Cold Spring Harbor Laboratory Press, Cold Spring Harbor, N.Y.). Plasmid DNA was isolated from Agrobacterium by a modification of the alkaline lysis procedure of Birnboim and Doly (Birnboim HC, Doly J (1979) Nucl. Acids Res. 7:1513–1523), in which an extra denaturing step was included by the addition of a NaOH-phenol solution (2×0.2N NaOH, 1× Tris-saturated phenol) to the alkaline lysate (1/10 vol.). Hybridization was carried out at 42° C. in 50% formamide, 5× SSC, and the hybridized filters were washed at 42° C. in 2× SSC, 0.1% SDS.

Plasmid Transfer to Agrobacterium Strains

Plasmids were routinely introduced into the Agrobacterium strains by electroporation, as described (Mozo T, Hooykaas PJJ (1991) Plant Mol. Biol. 16:917–918). Triparental matings according to Ditta et al. (supra) were used when a double cross-over was intended.

PCR Amplification of the Cre Gene

PCR was performed in a Biozym-PREM processor. The DNA isolated form 0.5 ml of an overnight culture of P1 containing E. coli cells was EcoRI digested (the cre gene has no EcoRI sites (Sternberg N, Sauer B, Hoess R, Abremski K (1986) J. Mol. Biol 187:197–212), and used for PCR in a final volume of 100 µl. The reaction mixture contained: 50 mM KCl, 10 mM Tris-HCl (pH 8.8), 1.5 mM $MgCl_2$, 100 µg/ml BSA, 50 µM of each nucleotide (Pharmacia), 0.45 µM of each primer and 5 U of Taq polymerase (Promega). Reactions were overlaid with 75 µl of mineral oil. The mixture war heated at 93° C. for 2 min to denature the DNA, cooled at 55° C. for 1 min to anneal the primers, and heated again to 72° C. for 1 min to initiate the amplification. The actual amplification took place during 20 cycles of 93° C.—1 min, 55° C.—1 min, 72° C.—1 min, followed by a final elongation step of 5 min at 72° C. The mixture was finally extracted twice with chloroform to remove the oil.

The primers were designed to obtain a final 5' SphI –3' BcORI cre gene, with no native promoter (Sternberg et al., supra). The sequence of the upstream primer was 5'-GGGCATGCGGAGTGTTAAATGTCC-3' (SEQIDNO: 1), and the downstream primer was 5'-GGGAATTCATGGCTAATCGCCATC-3' (SEQIDNO: 2) (start and stop codons are underlined).

LoxP Sequence

A 41 bp synthetic BamHI-EcoRI loxP sequence was constructed from the oligonucleotides: P1, 5'-GGATCCATAACTTCGTATAATGTATGCTATACGAAGTTATG-3'(SEQIDNO: 3), and P2, 5'-GAATTCATAACTTCGTATAGCATACATTATACGAAGTTATG-3' (SEQIDNO: 4).

EXAMPLE I

Obtention of Agrobacterium Strain MOG101

A helper plasmid conferring the *Agrobacterium tumefaciens* virulence functions derived from the octopine Ti-plasmid pTiB6 was constructed, MOG101. MOG101 is a *Agrobacterium tumefaciens* strain carrying a non-oncogenic Ti-plasmid from which the entire T-region was substituted by a bacterial Spectinomycin resistance marker from transposon Tn 1831 (Hooykaas et al., 1980 Plasmid 4, 64–75).

The Ti-plasmid pTiB6 contains two adjacent T-regions, TL (T-left) and TR (T-right). To obtain a derivative lacking the TL- and TR-regions, we constructed intermediate vector pMOG579. Plasmid pMOG621 is a pBR322 derivative, which contains the 2 Ti-plasmid fragments that are located to the left and right, outside the T-regions (FIG. 2). In pMOG579 the 2 fragments (shown in dark) were separated by a 2.5 kb BamHI-HindIII fragment from transposon Tn1831 (Hooykaas et al., 1980 Plasmid 4, 64–75) carrying the spectinomycin resistance marker (FIG. 2). The plasmid was introduced into *Agrobacterium tumefaciens* strain LBA1010 [C58-C9 (pTiB6)=a cured C58 strain in which pTiB6 was introduced (Koekman et al. (1982), Plasmid 7, 119–132) by triparental mating from E. coli, using HB101 8pRK2013) as a helper. Transconjugants were selected for resistance to Rifampicin (20 mg/l) and spectinomycin (250 mg/l). A double recombination between pMOG579 and pTiB6 resulted in loss of carbenicillin resistance (the pBR322 marker) and deletion of the entire T-region. Of 5000 spectinomycin resistant transconjugants, replica plated onto carbenicillin (100 mg/l) 2 were found sensitive. Southern analysis showed that a double crossing over event had deleted the entire T-region (not shown). The resulting strain was called MOG101. This strain and its construction is analogous to strain GV2260 (Deblaere et al. 1985, Nucl. Acid Res. 13, 4777–4788).

EXAMPLE II

Construction of pRL756 Harboring the Cre Gene on a Plasmid Unstable in Agrobacterium The PCR fragment containing the cre gene was digested with SphI and EcoRI and cloned into the polylinker site of plasmid pUC19 (FIG. 1). The resulting construct contains the cre-gene under the control of the lac promoter. The resulting pUC19-cre plasmid was subsequently cloned into the unique EcoRI site of the incP plasmid pNJ5000. The Cb marker of the pUC19 plasmid, allowing positive selection for the recombinant clones, made straightforward an otherwise highly difficult cloning step, given the large size (44 kb) and low copy number of the plasmid pNJ5000. The stability of the final cre-construct (pRL756) was checked in the Agrobacterium strain MOG1010. In these experiments, between 50% and 70% of the population lost the plasmid after 24 hours of growth in liquid medium in the absence of both carbenicillin and tetracycline, while pRL756 was stably maintained in the Agrobacterium cells when both antibiotics were included in the culture medium (data not shown).

EXAMPLE III

Construction of a pTi-loxP Disarmed Helper

An EcoRI loxP-Spc cassette was constructed in two steps in plasmid pIC20H (details of the cloning procedures are shown in FIG. 3). This cassette was subsequently cloned into the EcoRI site of plasmid pMOG621. This plasmid contains two fragments from pTiB6 which flank the T-DNA outside the left and right borders in the original pTiB6 and can therefore, be used as intermediate for T-DNA elimination or substitution by double homologous recombination at these two pTi fragments. The resulting plasmid pMOG622 was introduced by triparental mating into Agrobacterium strain LBA1010, and double recombinants in which the T-DNA had been exchanged by the loxP-Spc cassette were selected by resistance to spectinomycin and sensitivity to carbenicillin (indicating loss of the pBR322 vector part of pMOG622). The presence of the loxP-Spc cassette in the resulting pLBA1010 (δT-DNA)::loxP-Spc disarmed helper was checked by Southern blot (FIG. 9). This plasmid was called pAL1166 (see FIG. 3).

EXAMPLE III-A

Cre-mediated Cointegration Experiments

In order to determine whether the two plasmids described above can actually mediate loxP-site specific recombination, a third plasmid was constructed by cloning a kanamycin resistance gene into the EcoRI site of plasmid pRL753 (FIG. 3). The resulting plasmid pRL754 was used to check cointegrate formation after electroporation into Agrobacterium strains containing the loxP system by selection for $Km^r$ colonies suggesting that site-specific recombination has taken place. The results are discussed more extensively in Example III-B.

EXAMPLE III-B

Control Experiments and Evidence for Site-specific Cre Mediated Cointegration

A number of experiments were carried out to provide evidence that Cre-loxP mediated site-specific recombination accounted for cointegrate formation.

Figure 4:
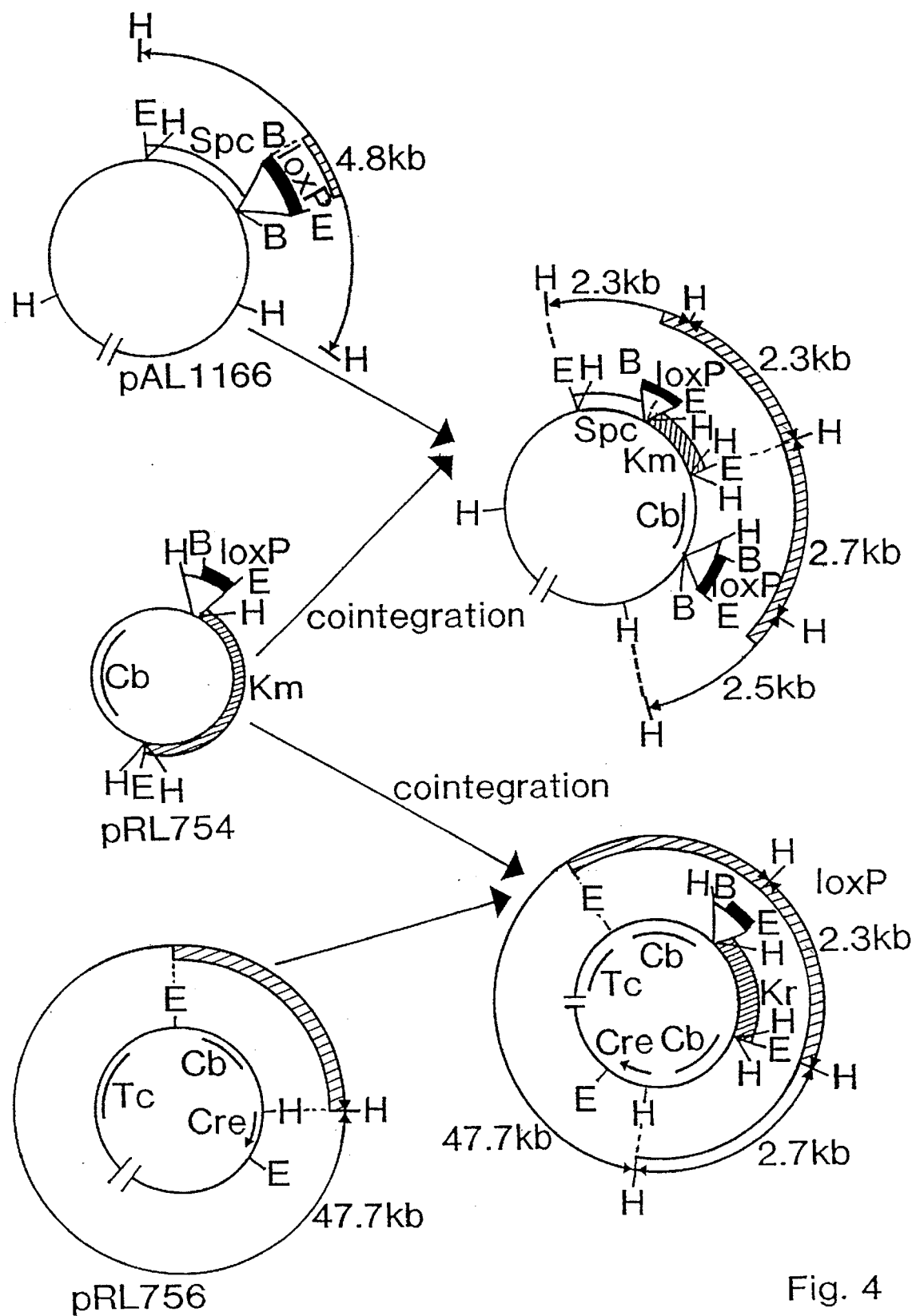
FIG. 4 schematically shows cointegration of pAL1166 and pRL754 via site-specific recombination of the loxP sites on both plasmids (upper right part); the lower part shows potential cointegration of pRL754 and pRL756 via homologous recombination, due to the presence of regions of homology between these two plasmids. The latter event, if significant at all, can be avoided if the cre plasmid and the plasmid harboring the DNA to be introduced share no homology or as little as possible.
Figure 5:
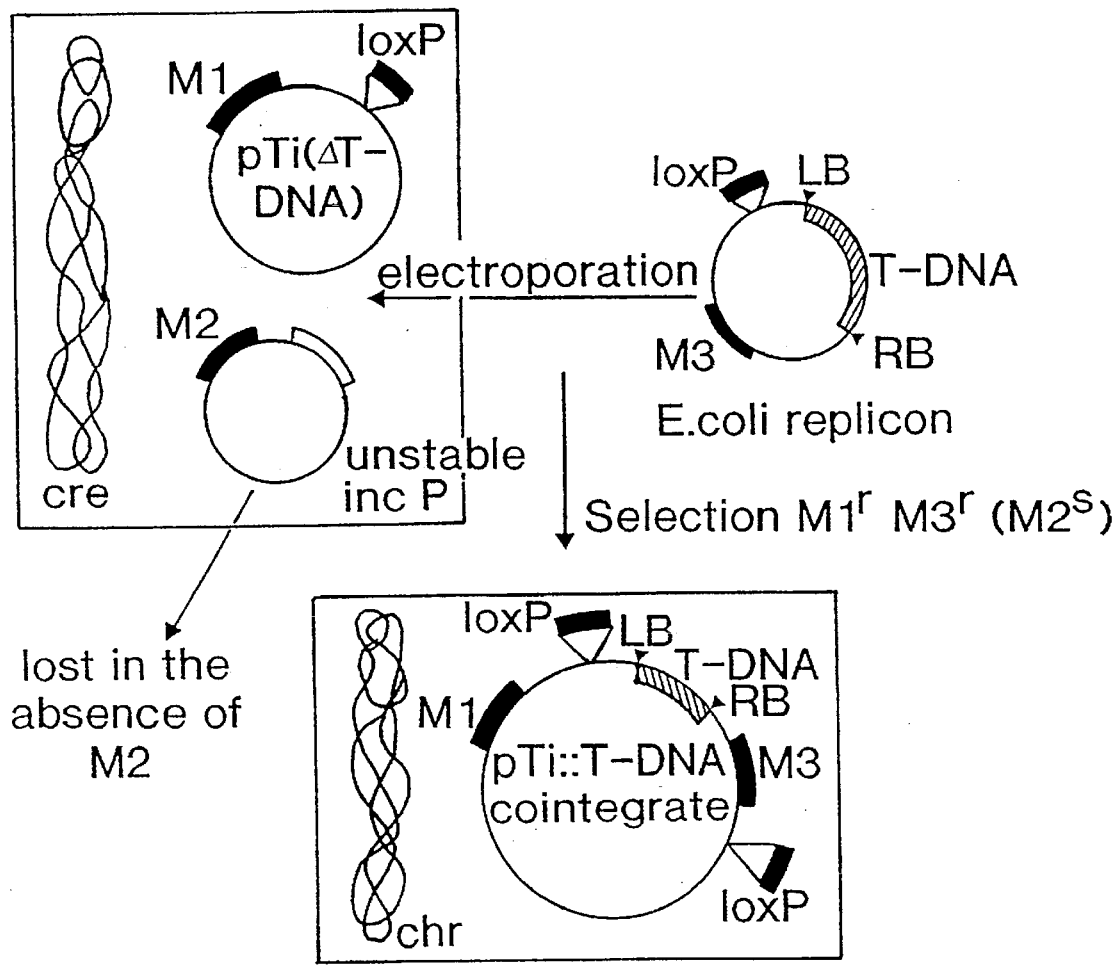
FIG. 5 represents a generalized scheme for obtaining cointegrates which contain a manipulated T-region for transfer to plant cells; the T-DNA comprises a gene of interest, and, if desired, a marker gene allowing for selection or screening of transformed plant cells. chr=Agrobacterium chromosome; M1 marker gene 1 for selection in Agrobacterium; pTi(δT-DNA) a disarmed (deleted T-DNA) Ti-plasmid harboring vir-functions; M2 marker gene 2 for selection in Agrobacterium; M3 marker gene 3 for selection in Agrobacterium; M1$^r$M3$^r$(M2$^s$) phenotype resistance to marker 1 and 3, and sensitivity to marker 2; LB=left border; RB=right border; incP=plasmid of incompatibility group P.

Besides the strain containing both the pTi-loxP disarmed helper pAL1166 and the Cre-plasmid pRL756, strains containing only pAL1166 or a normal pTi helper plus pRL756 were used as control. In addition, a strain in which pRL757 had been integrated into MOG101 by single recombination at the Spc marker gene was included in the experiments in order to compare the efficiency of the loxP-Cre mediated and the normal homologous recombination processes. In a parallel experiment and as a way to assess that all the Agrobacterium strains used had similar levels of competence for DNA uptake, the same strains were also electroporated with the $Km^r$ plasmid pBIN19. The results of these experiments are presented in Table 1A. As can be seen from the table, the strains used did not differ significantly in their competence for DNA uptake of the control plasmid pBIN19. However, none or a just a single $Km^r$ transformant was obtained when pRL754 was electroporated into the strains that did not contain any of the loxP-Cre elements or only contain the loxP site as homologous recombination between the common pIC20H-loxP sequences was apparent when pRL754 was introduced into the strain containing pRL757 integrated into the pTi plasmid. A similar frequency of homologous recombination was observed for the strain containing pRL756 and no loxP site. In this case, the incoming plasmid and the resident pRL756 have in common the pUC replication and Cb regions (FIG. 4). The homology between these two plasmids posed an important problem to assess loxP-Cre site-specific recombination in the strain containing both the pAL1166 helper and pRL756. Although a slightly higher transformation frequency was obtained by electroporation of pRL754 into that strain, this increase was not enough to be attributed to the addition of loxP-Cre specific recombination events to the already shown highly efficient pUC-Cb mediated homologous recombination, considering that this strain also resulted in more $Km^r$ transformants when electroporated with pBIN19. An indirect approach was followed in order to check whether loxP-Cre site-specific recombination had actually occurred. The $Km^r$ transformants obtained by electroporation of pRL754 into the strains containing pRL756 and either the normal helper pMOG101 or the pTi-loxP helper pAL1166 were separately pooled, grown overnight in liquid cultures with and without kanamycin, and plated in media without antibiotics, with kanamycin and with tetracycline to assay for the stability of the markers (Table 2). These experiments showed that, when growing in antibiotic-free medium, Km and Tc were lost at the same rate (12%) in the case of the cells which did not include the loxP site, thus indicating that Km is linked to Tc in the unstable pRL756 plasmid. In contrast, in the case of the transformants obtained with the pAL1166 helper containing strain, Tc was lost in a 91% of the cells, while the rate for the Km loss was only of 38%. In agreement with that, when this second group of transformants was grown in Km, only 13.5% of the cells retained the Tc marker. These results, showing that there is no linkage between Km and tc markers in the $Km^r$ transformants obtained by electroporation of pRL753, demonstrate that the incoming plasmid is not cointegrated with pRL756 and suggest that the Km resistance is due to integration of pRL754 into pAL1166 by loxP-Cre mediated recombination.

The cointegration between the incoming plasmid and pRL756 may have also occurred, but since this would give rise to different loxP containing plasmids in the same cell, the situation would not be stable, unless the Cre plasmid pRL756 or a putative pRL756::pRL754 cointegrate plasmid would have been lost. This instability is also suggested by the higher rate of $Km^r$ loss from this group of transformants when growing in antibiotic-free medium (38% vs. 12% in the loxP absent transformants).

In order to more definitively assess the loxP-Cre site-specific recombination in our system, the above described electroporation experiments were repeated in a RecA⁻ background (Table 1B), in which no homologous recombination events should occur. As expected, the transformation frequency in the case of the strain containing pRL757 integrated into the pTi was now reduced to the levels obtained when no homologous sequences or only the small loxP site were involved (this levels can be assimilated to the frequency of spontaneous mutations). However, despite the RecA⁻, the transformation frequencies in both strains containing pRL756 was again similar, independent of the presence of the loxP site. This unexpected result indicates that the Cre protein may mediate recombination at sites different from the loxP sequence. In an attempt to discriminate between these two types of Cre-mediated recombination, the $Km^r$ transformants obtained with both the loxP-present and absent strains were directly checked, without further culturing, for the presence of the Km and Tc resistance markers. While all MOG101(pRL756) transformants were $Km^r Tc^r$, 50% of the pAL1166 transformants were $Km^r Tc^s$, thus indicating that pRL756 had been lost shortly after the loxP-Cre mediated cointegration of pRL754 into the pAL1166. The remaining 50% $Km^r Tc^r$ transformants would likely include only pRL754::pRL756 cointegrates because of the stability problems that the coexistence of different loxP containing plasmids in the same cell in the presence of the cre protein may cause, as discussed. The recombination events were checked by Southern blot analysis of four representatives of each type ($Tc^r$ and $Tc^s$) of transformants (FIG. 4). The plasmid DNA isolated from those transformants was HindIII digested and hybridized with labelled pRL754. In the case of all $Tc^r$ transformants checked, three bands corresponding with the HindIII fragments of a putative pRL757::pRL754 cointegrate (FIG. 8) were observed, together with the HindIII pAL1166 fragment which contains the loxP sequence (FIG. 3). The stronger hybridization signal in the upper band corresponding to the 44 kb pRL756 is likely due to the presence of non-cointegrated copies of this plasmid, since incP plasmids can exist in several copies per cell and the cointegration of the Km-containing incoming plasmid in only one of them should be enough to confer Km resistance. In the $Tc^s$ transformants this upper band was absent, as like the pAL1166 fragment containing the loxP site. Three bands were observed in this case corresponding to the expected HindIII fragments of a pAL1166::pRL754 cointegrate obtained by recombination at the loxP site (FIG. 4). Again there is a difference in the relative intensity of the hybridizing bands which can be attributed to the integration of several copies of the incoming plasmid into the pTi-loxP helper plasmid (pAL1166).

These results clearly show that loxP-Cre mediated site-specific cointegrate formation works efficiently in the Agrobacterium cells and is a useful alternative for obtaining cointegrates using homologous recombination.

EXAMPLE IV

Construction of a pTi::T-DNA Cointegrate

Figure 6:
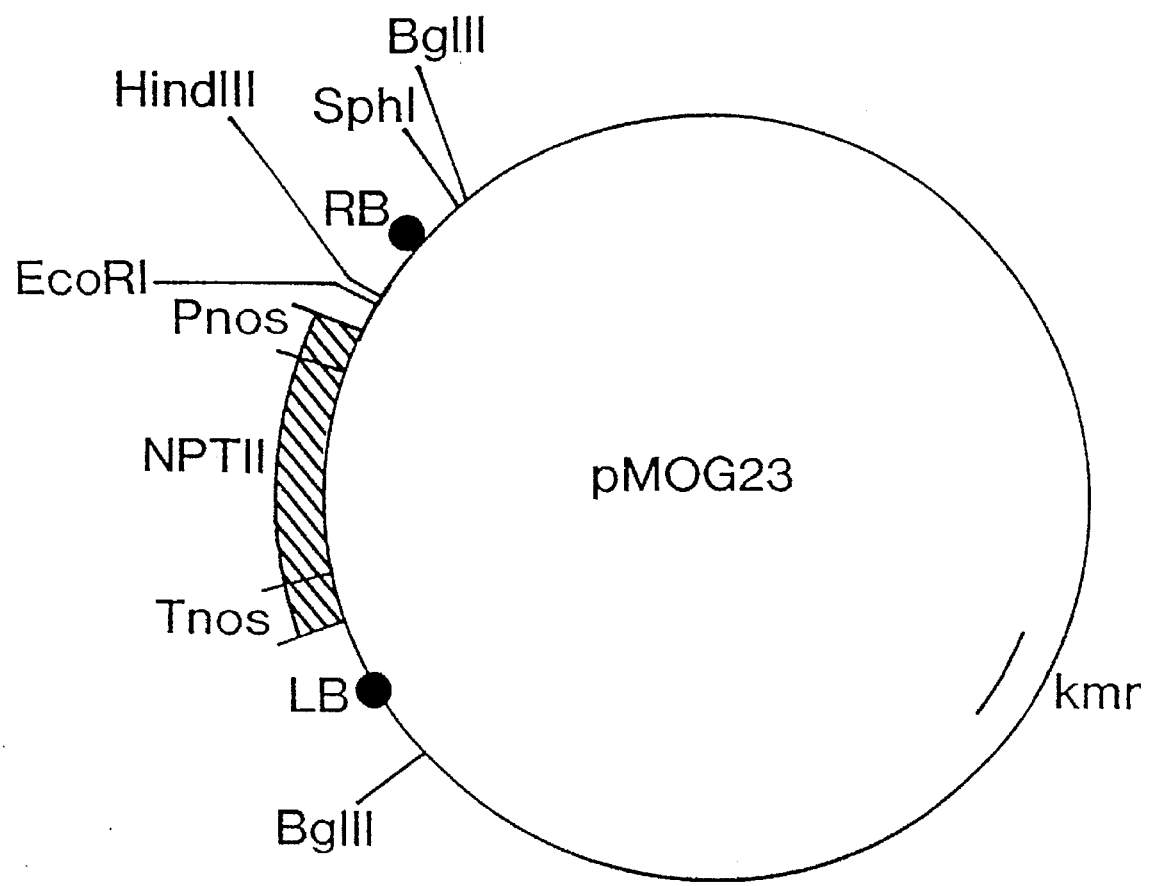
FIG. 6 is a diagram of pMOG23, harboring a chimeric kanamycin resistance gene for selection in plants, comprising promoter region from the nopaline synthase (nos) gene of Agrobacterium tumefaciens, which is capable of controlling gene expression in plant cells, a structural coding sequence encoding the neomycin phosphotransferase, and the terminator region of the nos-gene.

Having established the process of loxP-Cre mediated cointegrate formation in Agrobacterium, we carried out experiments to introduce a modified T-region into the disarmed loxP-helper plasmid pAL1166. To this aim we subcloned the T-region fragment as contained on the binary vector pMOG23 (in *E. coli* K-12 strain DH5α, deposited at the Centraal Bureau voor Schimmelcultures on Jan. 29, 1990 under accession number CBS 102.90). As shown in FIG. 6, the entire T-region of pMOG23, carrying a chimeric NPTII gene between its left and right borders, is contained on a BglII-restriction fragment. This fragment was subcloned into plasmid pRL754 (Example III-A3) linearized with the enzyme BamHI.

Figure 7:
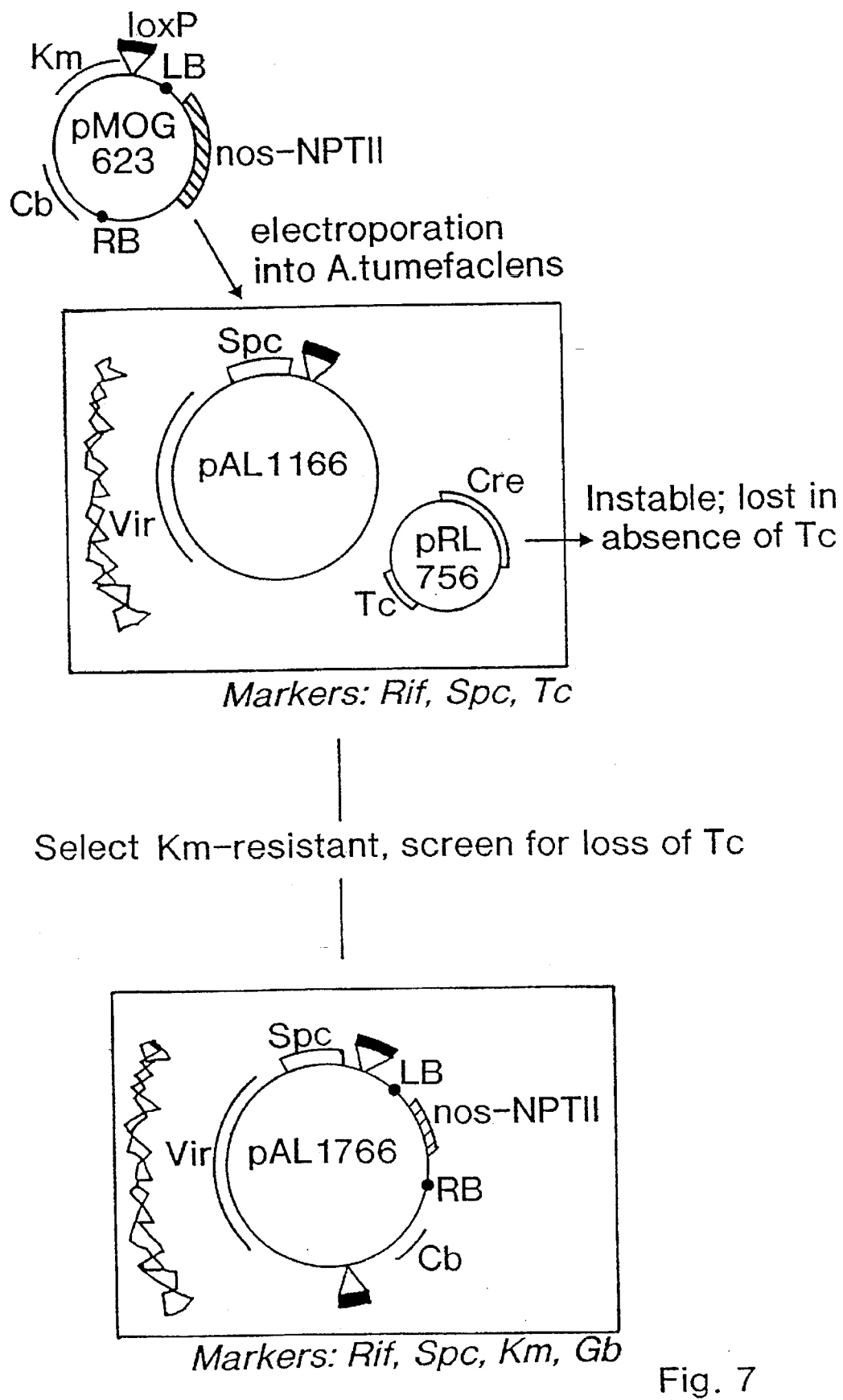
FIG. 7 diagrammatically illustrates the construction of pAL1766, a site-specific cointegrate, harboring the chimeric plant expressible kanamycin resistance gene flanked on both sides by T-DNA borders, and the virulence functions from pAL1166. This plasmid was used to transfer the kanamycin resistance gene to tobacco cells and regenerate transformed tobacco plants.

The resulting plasmid pMOG623 was integrated into pAL1166 as shown in FIG. 7. The Agrobacterium strain carrying pAL1166 and pRL756 (Example II) was electroporated with plasmid pMOG623 selecting for kanamycin resistance. This was followed for screening for loss of $Tc^R$, indicative for loss of pRL756. This process resulted in the formation of of a pAL1166-pMOG623 cointegrate, called pAL1766. Its structure is shown in FIG. 7.

EXAMPLE V

Plant Transformation

The Agrobacterium strain pAL1766 was used for transformation of tobacco plants, next to Agrobacterium strain MOG101 carrying pMOG23. This was done to compare the transformation capability of strains constructed via loxP-Cre mediated cointegrate formation with strains carrying binary vectors.

Transformation of tobacco (*Nicotiana tabacum* cv. Petit Havana SR1) was done via cocultivation of 50 leaf discs according to the procedure of Horsch et al. (Horsch et al., (1985), Science 227, 1229–1231). In experiments with both strains, the leaf discs were cocultivated with bacteria grown to $OD_{550}$ of 0.5 during 48 hrs, and transferred to selective media (100 mgs/l kanamycin). After 4–6 weeks shoots were obtained and assayed for proper rooting on kanamycin (100 mgs/l), transferred to soil and allowed to selfpollinate and set seed. Seeds from individual transformants were pooled and germinated on kanamycin (200 mgs/l). From these experiments out of 50 leaf discs a total of 25–30 transgenic plants was recovered. No differences were observed in numbers or appearance of plants obtained via either vector system.

Deposit of Microorganisms

*Agrobacterium tumefaciens* strain LBA1166 harboring pAL1166 has been deposited at the NCC, Julianalaan 67, Delft, The Netherlands, on Feb. 26, 1992, under deposit number cbs 147.92.

---

We claim:

1. An Agrobacterium strain comprising a structural DNA sequence encoding a site-specific recombinase that is Cre recombinase and a DNA sequence linked thereto which operationally controls expression of said Cre recombinase, said strain further comprising a first recombination site.

2. An Agrobacterium strain according to claim 1, wherein said recombination site is located on a plasmid.

3. An Agrobacterium strain according to claim 2, wherein said plasmid is a helper plasmid comprising vir-functions.

4. An Agrobacterium strain according to claim 3, wherein said helper plasmid does not contain T-DNA borders.

5. An Agrobacterium strain according to claim 1, wherein said first recombination site is a loxP site.

6. An Agrobacterium strain according to claim 1, wherein said structural DNA sequence encoding Cre is on a plasmid that is unstable in said Agrobacterium strain.

7. An Agrobacterium strain according to claim 6, wherein said structural coding sequence is under the control of the lac promoter from *E. coli*.

8. A method for producing a site-specific cointegrate comprising introducing into the Agrobacterium strain of claim 1 a DNA molecule comprising a second recombination site compatible with said first recombination site, and causing said strain to express the Cre recombinase so as to promote recombination between said first and second recognition sites whereby to produce the site-specific cointegrate.

9. A method according to claim 8, further comprising the steps of effecting a reduced production of the site-specific recombinase, and selecting Agrobacterium strains comprising the site-specific cointegrate.

10. A site-specific cointegrate obtained using the method of claim 9.

11. A site-specific cointegrate obtained using the method of claim 8.

12. A method according to claim 8 wherein said Agrobacterium strain comprises vir-functions and wherein the DNA molecule also comprises a DNA sequence not naturally present in a plant cell, said DNA sequence not naturally present being positioned on the DNA molecule between a left and a right T-DNA border.

13. A method according to claim 8 wherein said Agrobacterium strain comprises vir-functions and wherein the DNA molecule comprising a second recombination site contains DNA not naturally present in a plant cell, said DNA not naturally present being positioned on the DNA molecule with respect to a right T-DNA border so as to allow said vir-functions to mediate co-transfer of said DNA not naturally present with said right T-DNA border.

14. A site-specific cointegrate obtained using the method of claim 13.

15. Agrobacterium strains comprising the site-specific cointegrate of claim 8.

16. A method for producing a site-specific cointegrate in the Agrobacterium strain of claim 1, with said Cre recombinase mediating integration of first and second DNA molecules when the molecules respectively comprise first and second recognition sites, the method comprising:

a) introducing the first and second DNA molecules into the Agrobacterium strain; and b) causing said strain to express the Cre recombinase so as to promote recombination between said first and second recognition sites whereby to produce a cointegrate of said first and second DNA molecules in said Agrobacterium strain without homologous recombination.

17. A method according to claim 16 wherein said first and second DNA molecules are free of repetitive DNA sequences that can promote homologous recombination.

18. A method according to claim 16 wherein the Agrobacterium strain is a rec⁻ strain.

19. A method according to claim 16 wherein said second DNA molecule comprises DNA not naturally present in a plant cell and at least a right T-DNA border, said Agrobacterium strain comprising vir-functions to mediate transfer of DNA in the cointegrate to the plant cell, said DNA not naturally present being positioned in the second DNA molecule with respect to the right T-DNA border such that transfer to the plant cell of DNA in the cointegrate mediated by said vir-functions includes transfer of said DNA not naturally present.

20. A method according to claim 19 further comprising:

c) contacting cells of a plant with said Agrobacterium strain so as to cause transfer to the plant of said DNA not naturally present; and d) selecting a plant cell to which said DNA not naturally present has been transferred.

* * * * *

UNITED STATES PATENT AND TRADEMARK OFFICE
CERTIFICATE OF CORRECTION

PATENT NO. : 5,635,381
DATED : June 3, 1997
INVENTOR(S) : Paul J.J. HOOYKAAS
              Teresa MOZO It is certified that error appears in the above-indentified patent and that said Letters Patent is hereby corrected as shown below:

On the title page, item [73], Assignee

ADD -- RIJKSUNIVERSITEIT TE LEIDEN
           LEIDEN, NETHERLANDS --

Signed and Sealed this

Sixth Day of July, 1999

*Attest:*

*Attesting Officer*

Q. TODD DICKINSON

*Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: cDNA ( i i i ) HYPOTHETICAL: Yes ( x i ) SEQUENCE DESCRIPTION: SEQ ID NO:1:

```
GGGCATGCGG  AGTGTTAAAT  GTCC                                                    24
```

( 2 ) INFORMATION FOR SEQ ID NO:2:

( i ) SEQUENCE CHARACTERISTICS:
        ( A ) LENGTH: 24
        ( B ) TYPE: Nucleic Acid
        ( C ) STRANDEDNESS: Single
        ( D ) TOPOLOGY: Linear ( i i ) MOLECULE TYPE: cDNA ( i i i ) HYPOTHETICAL: Yes ( x i ) SEQUENCE DESCRIPTION: SEQ ID NO:2:

```
GGGAATTCAT  GGCTAATCGC  CATC                                                    24
```

( 2 ) INFORMATION FOR SEQ ID NO:3:

( i ) SEQUENCE CHARACTERISTICS:
        ( A ) LENGTH: 41
        ( B ) TYPE: Nucleic Acid
        ( C ) STRANDEDNESS: Single
        ( D ) TOPOLOGY: Linear ( i i ) MOLECULE TYPE: cDNA ( i i i ) HYPOTHETICAL: Yes ( x i ) SEQUENCE DESCRIPTION: SEQ ID NO:3:

```
GGATCCATAA  CTTCGTATAA  TGTATGCTAT  ACGAAGTTAT  G                               41
```

( 2 ) INFORMATION FOR SEQ ID NO:4:

( i ) SEQUENCE CHARACTERISTICS:
        ( A ) LENGTH: 41
        ( B ) TYPE: Nucleic Acid
        ( C ) STRANDEDNESS: Single
        ( D ) TOPOLOGY: Linear ( i i ) MOLECULE TYPE: cDNA ( i i i ) HYPOTHETICAL: Yes ( x i ) SEQUENCE DESCRIPTION: SEQ ID NO:4:

```
GAATTCATAA  CTTCGTATAG  CATACATTAT  ACGAAGTTAT  G                               41
```